United States Patent [19]

Burgoyne, Jr. et al.

[11] Patent Number: 4,908,480

[45] Date of Patent: * Mar. 13, 1990

[54] PROCESS FOR PRODUCING MONO-ORTHO-ETHYL-ANILINE USING SILICA-ALUMINA CATALYSTS

[75] Inventors: William F. Burgoyne, Jr., Emmaus, Pa.; Dale D. Dixon, Venice, Fla.

[73] Assignee: Air Products and Chemicals, Inc., Allentown, Pa.

[*] Notice: The portion of the term of this patent subsequent to Apr. 26, 2005 has been disclaimed.

[21] Appl. No.: 220,040

[22] Filed: Jul. 15, 1988

[51] Int. Cl.$^4$ .............................................. C07C 51/16
[52] U.S. Cl. ................................................... 564/409
[58] Field of Search ........................................ 564/409

[56] References Cited

U.S. PATENT DOCUMENTS

| | | | |
|---|---|---|---|
| 2,194,079 | 3/1940 | Smith et al. | 260/576 |
| 4,351,951 | 9/1982 | Baizer et al. | 560/186 |
| 4,740,620 | 4/1988 | Dixon et al. | 564/409 |

FOREIGN PATENT DOCUMENTS

| | | | |
|---|---|---|---|
| 663698 | 5/1963 | Canada | 564/409 |
| 1406739 | 6/1965 | France | 564/409 |
| 421791 | 12/1934 | United Kingdom | 564/409 |
| 846226 | 8/1960 | United Kingdom | 564/409 |

*Primary Examiner*—Richard L. Raymond
*Assistant Examiner*—Raymond Covington
*Attorney, Agent, or Firm*—Russell L. Brewer; James C. Simmons; William F. Marsh

[57] ABSTRACT

This invention relates to a process for producing mono-ortho-ethyl- aniline in high selectivity and at high conversion using a silica-alumina catalyst. The reaction is carried out using a fixed bed reactor. Diethylaniline derivatives are avoided by maintaining preselected mole ratios of ethylene to aniline, preselected temperatures and preselected reaction times.

4 Claims, 2 Drawing Sheets

PROCESS FOR PRODUCING MONO-ORTHO-ETHYL-ANILINE USING SILICA-ALUMINA CATALYSTS

TECHNICAL FIELD

This invention pertains to a process for producing mono-ortho-ethyl-aniline at high selectivity and at high conversion using a silica-alumina catalyst.

BACKGROUND OF THE INVENTION

The alkylation of aromatic amines by the reaction of the aromatic amine with an olefin in the presence of a catalyst system is known. Patents which illustrate aromatic amine alkylation processes using a heterogeneous catalyst system comprising silica-alumina catalysts are as follows:

British Patent 421,791 discloses the reaction of N-alkylated aromatic amines to ring alkylated aromatic amines by effecting isomerization in the presence of activated hydrosilicates.

French Patent 1,406,739 discloses ring alkylation of aromatic amines and other aromatic compounds by contacting the aromatic amine with an olefin in the presence of a crystalline alumino-silicate. Aniline and diphenylamine are represented as examples of aromatic hydrocarbon suited for alkylation.

Canadian Patent 663,698 discloses para-alkylation of aromatic amines, typically aniline derivatives, by contacting aniline with an olefin in the presence of a silica-alumina-type catalyst. Anilineisobutylene reactions are carried out at temperatures from about 200°–330° C. with temperatures of 240°–260° C. being preferred.

U.S. Pat. No. 4,351,951 discloses a process for preparing aromatic amines by reacting the aromatic amine with the primary or secondary alcohol in the presence of a catalyst containing iron oxides.

U.S. Pat. No. 4,740,620 discloses a process for alkylating aromatic amines by reaction with olefin in the presence of highly acidic crystalline alumina-silicates.

British Patent 846,226 discloses a process for the alkylation of aniline and phenyl amines by reaction with isobutylene in liquid phase at temperatures between 150° and 300° C. in the presence of activated, substantially neutral bleaching earths of the montmorillonite type.

Lavroski, et al., in an article *Catalytic Alkylation of Aniline by n-Butene* shows the reaction of aniline with n-butene in the presence of a silica-alumina catalyst.

U.S. Pat. No. 2,194,079 shows the reaetion of diphenylamine with cyclohexene in the presence of an acid-activated bleaching earth.

SUMMARY OF THE INVENTION

This invention relates to an improved process for producing mono-ortho-ethyl aniline by the alkylation of aniline with ethylene in the presence of a silica-alumina catalyst system. As noted in the prior art, aromatic amines, including aniline, have been alkylated with olefins using silica-alumina catalyst systems. However, a mixed reaction product effluent was obtained. The improvement for producing mono-ortho-ethyl aniline as opposed to di-ortho-ethyl aniline in the form of ring di-ethyl derivatives as well as a mixture of ring and N-alkylated di-ethyl aniline derivatives involves careful reaction control to minimize by-product formation in the form of di-ethyl derivatives of aniline and carrying out the reaction in a fixed bed catalytic reactor. The reaction is carried out by contacting a feedstock of aniline and ethylene where the molar ratio of aniline to ethyl is from 2 to 10:1. The temperature is maintained from 250° to 450° C. and the pressure is maintained from 500 to 2000 pounds per square inch. The reaction is carried out in a fixed bed reactor, in contrast to a stirred, tank reactor, and the space velocity based upon aniline feed to the reactor is from 0.05 to 0.5 cc's per hour per cc volume catalyst (LSHV).

DRAWINGS

FIG. 1 plots product ratio versus reaction temperature for the reaction of ethylene with aniline over silica-alumina at 6.5% $Al_2O_3$.

FIG. 2 is a plot of product ratio versus reaction temperature for the reaction of ethylene with aniline over silica-alumina at 13% $Al_2O_3$.

DETAILED DESCRIPTION OF THE INVENTION

Figure 1:
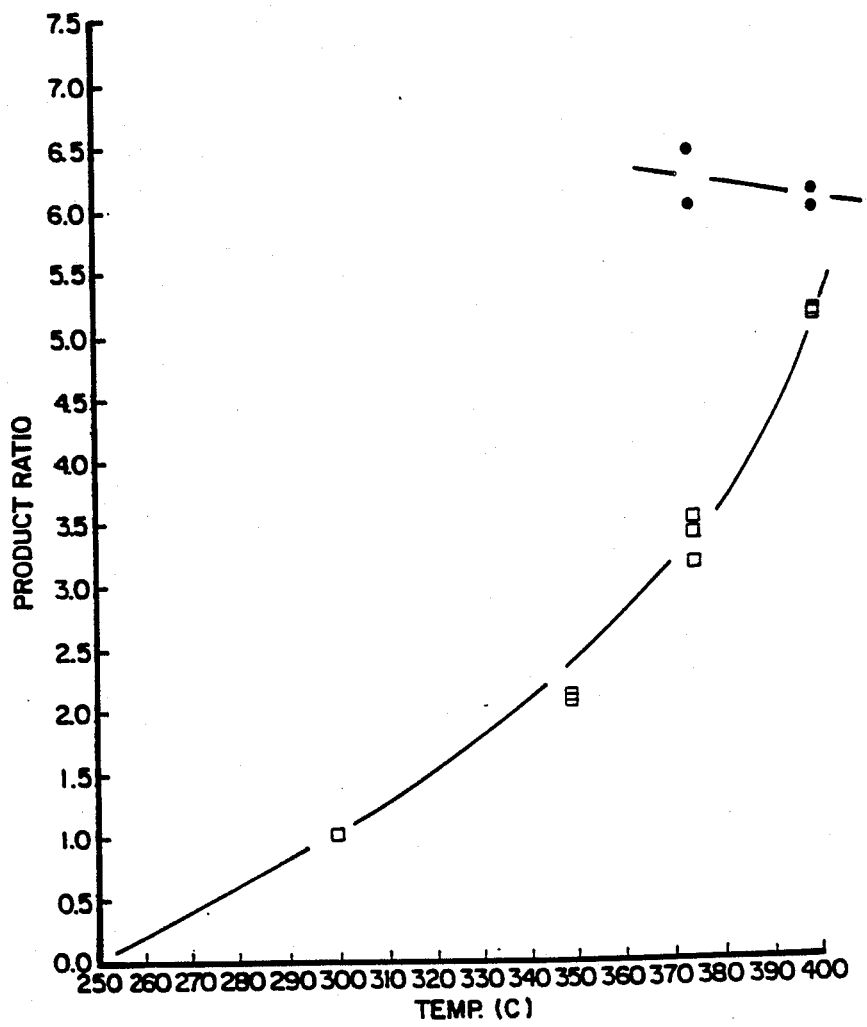
Figure 2:
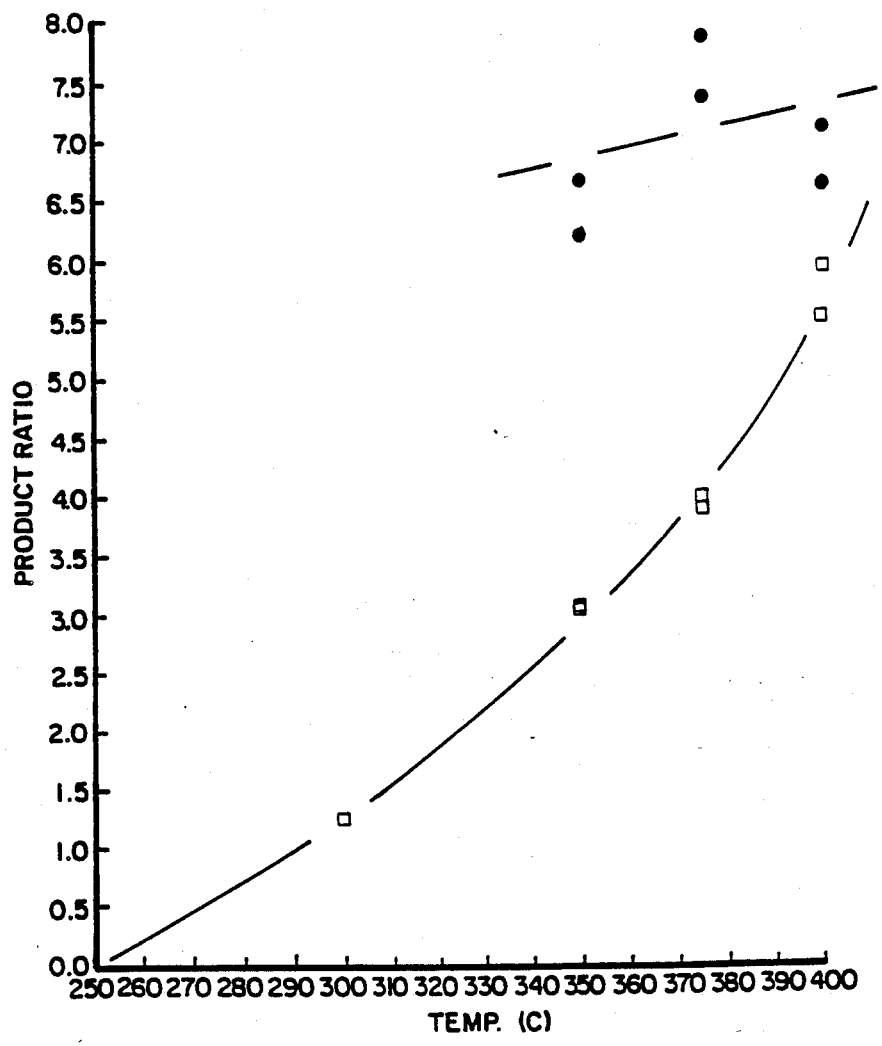

In the alkylation of aniline with ethylene, a variety of products are produced which include N,N-alkylated anilines to ring alkylated aniline derivatives to a combination of N and ring alkylated aniline derivatives or polyalkylated ring aniline derivatives. Because ethylene is readily reacted with aniline, and a variety of products are produced by the reaction, there is a need to maximize the amount of mono-ortho-ethyl-aniline where the ethyl group is ortho to the amine without generating other by-products. The N-alkylated derivatives are difficult to separate from the ring-alkylated aniline derivatives and the di-ethyl-butyl derivatives of aniline must be decomposed in order to recover reactants.

It has been found in the practice of this invention that minimal amounts of di-ethyl derivatives of aniline can be produced by the reaction of ethylene with aniline in the presence of a silica-alumina catalyst and when the reaction is carried out in a fixed bed reactor. The catalyst system is highly acidic and a catalyst having a silica content from 70 to 85% by weight should be utilized. Although other oxides can be present in the catalyst system, e.g., magnesia, a catalyst system having essentially silica and alumina is preferred as such catalyst has the highest acidity. To enhance catalytic activity of the silica-alumina the catalyst can also be activated by removing alkali or alkaline earth metal oxides from the catalyst systems. That technique is referred to as activation and such activations can be accomplished by contacting the catalyst system with acid and recovery undissolved silica-alumina catalysts.

To effect high conversion at high selectivity, the reaction is carried out in a fixed bed catalytic reactor. A high rate of flow is maintained through the catalyst bed to minimize the effect of temperature excursion in the bed which may result in higher levels of di-ethyl derivatives of aniline in the reaction product. A liquid hourly space velocity of from 0.05 to 0.5 hours$^{-1}$ is maintained and preferably the liquid hour space velocity is from 0.1 to 0.25 hours$^{-1}$. The reaction temperature in the catalyst bed is maintained from about 300° to 375° C. When the temperature falls below about 250° C., insufficient conversion of aniline to ring alkylated aniline derivative is produced leaving unreacted aniline or higher concentrations of N-tert-butyl aniline in the reactor effluent. When the temperature above about 400° C. is employed or there are temperature excursions within the fixed bed catalytic reactor which results in localized temperatures above about 400° C., one may experience higher productions of para-ethyl aniline, and diphenylamine as well as aniline degradation products.

The mole ratio of ethylene to aniline in the initial reaction zone is maintained at a level from about 2 to 10 moles ethylene per mole aniline. This mole ratio permits conversion to be carried out at a level from about 40 to 60% based upon the moles of aniline present in the reactor feed. (N-ethyl derivatives of aniline being equivalent to 1 mole of unreacted aniline.) When the mole ratio falls below about 2 there is insufficient conversion of the aniline to product and when the mole ratio is above about 10 to 1 there is a tendency to convert some of the aniline to di-ethyl aniline.

The following examples are provided to illustrate various embodiments of the invention and are not intended to restrict the scope thereof.

EXAMPLE 1

Aniline and ethylene were pumped as liquids over a catalyst bed of silica and alumina held in a tube reactor and reacted. The bed contained 12 cc of catalyst and the catalyst contained 93.5% silica and 6.5% alumina.

Table 1 provides reaction conditions and analytical analysis of the reaction product. In Table I, N-ET refers to N-ethyl-aniline; 2-ET refers to 2-ethylaniline; 4-ET refers to 4-ethyl-aniline 2,6-di-ET refers to 2,6-diethylaniline and O/P refers to the ortho/para ratio.

The above procedure was repeated except that the catalyst contained 87% silica and 13% alumina. Table 2 sets forth the conditions and results.

TABLE 1

Aniline/ethylene over 6.5% $Al_2O_3/SiO_2$

| Run | Temp. C | Pres. PSIG | Molar Ratio N/R | LHSV (HR-1) | % Conv. Aniline | % Sel. N-ET | % Sel. 2-ET | % Sel. 4-ET | % Sel. 2,6-DI-ET | % Sel. PH2NH | o/p Ratio | Ring/N Ratio |
|---|---|---|---|---|---|---|---|---|---|---|---|---|
| 1 | 250 | 912 | 0.1 | 0.25 | 0.01 | 0.00 | 0.00 | 0.00 | 0.00 | 0.00 | | |
| 2 | 300 | 926 | 0.1 | 0.25 | 1.78 | 50.23 | 49.77 | 0.00 | 0.00 | 0.00 | | 0.99 |
| 3 | 300 | 935 | 0.1 | 0.25 | 1.74 | 50.22 | 49.78 | 0.00 | 0.00 | 0.00 | | 0.99 |
| 4 | 350 | 906 | 0.1 | 0.25 | 7.09 | 25.09 | 53.16 | 0.00 | 0.00 | 21.75 | | 2.11 |
| 5 | 350 | 907 | 0.1 | 0.25 | 6.97 | 24.98 | 52.88 | 0.00 | 0.00 | 22.14 | | 2.11 |
| 6 | 350 | 901 | 0.1 | 0.25 | 7.20 | 26.26 | 54.47 | 0.00 | 0.00 | 19.27 | | 2.07 |
| 7 | 375 | 903 | 0.1 | 0.25 | 13.82 | 19.86 | 54.75 | 7.63 | 0.00 | 17.76 | 7.18 | 3.14 |
| 8 | 375 | 897 | 0.1 | 0.25 | 11.63 | 20.01 | 58.64 | 9.14 | 0.00 | 12.21 | 6.42 | 3.39 |
| 9 | 375 | 903 | 0.1 | 0.25 | 11.44 | 17.21 | 51.84 | 8.64 | 0.00 | 22.28 | 5.98 | 3.51 |
| 10 | 400 | 906 | 0.1 | 0.25 | 20.91 | 11.40 | 49.96 | 8.37 | 2.93 | 18.87 | 5.97 | 5.11 |
| 11 | 400 | 906 | 0.1 | 0.25 | 18.87 | 12.39 | 54.21 | 8.91 | 2.93 | 21.57 | 6.08 | 5.09 |

TABLE 2

Aniline/ethylene over 13% $Al_2O_3/SiO_2$

| Run | Temp. C | Pres. PSIG | Molar Ratio N/R | LHSV 1/H | % Conv. Aniline | % Sel. N-ET | % Sel. 2-ET | % Sel. 4-ET | % Sel. 2,6-DI-ET | % Sel. PH2NH | o/p Ratio | Ring/N Ratio |
|---|---|---|---|---|---|---|---|---|---|---|---|---|
| 1 | 250 | 807 | 0.1 | 0.25 | 1.19 | 99.35 | 0.65 | 0.00 | 0.00 | 0.00 | | 0.01 |
| 2 | 300 | 826 | 0.1 | 0.25 | 5.28 | 37.31 | 47.78 | 0.00 | 0.00 | 15.21 | | 1.27 |
| 3 | 300 | 826 | 0.1 | 0.25 | 4.42 | 43.92 | 56.08 | 0.00 | 0.00 | 0.00 | | 1.28 |
| 4 | 350 | 831 | 0.1 | 0.25 | 20.65 | 20.37 | 54.49 | 8.73 | 4.07 | 9.10 | 6.24 | 3.10 |
| 5 | 350 | 836 | 0.1 | 0.25 | 20.44 | 20.23 | 55.03 | 8.24 | 3.91 | 8.90 | 6.67 | 3.12 |
| 6 | 375 | 824 | 0.1 | 0.25 | 36.29 | 14.20 | 50.37 | 6.82 | 7.46 | 7.02 | 7.39 | 4.03 |
| 7 | 375 | 828 | 0.1 | 0.25 | 36.23 | 14.59 | 50.87 | 6.47 | 7.62 | 6.95 | 7.86 | 3.93 |
| 8 | 400 | 825 | 0.1 | 0.25 | 52.31 | 8.40 | 43.50 | 6.57 | 10.16 | 5.97 | 6.62 | 5.96 |
| 9 | 400 | 815 | 0.1 | 0.25 | 53.02 | 8.94 | 43.47 | 6.12 | 10.40 | 5.31 | 7.10 | 5.55 |

Comments on Data
The above data show that significant conversion has been obtained at reaction temperatures about 300° C. At higher temperatures of 350 to about 375° C. conversion increased with excellent selectivity to 2-ethylaniline. Modest levels of 4-ethylaniline were produced as well as some level of diphenylamine. At the 400° C. level conversion began to fall and increased amounts of 2,6-diethylaniline was produced.

What is claimed:

1. In a process for reacting aniline with ethylene to form a ring alkylated aniline, said reaction being carried out in the presence of an acidic catalyst, the improvement for selectivity forming monoethyl aniline where the ethyl group is ortho to the amine at high conversion which comprises:

reacting aniline with ethylene; and effecting said reaction in the presence of a silica-alumina catalyst maintained in a fixed bed catalytic reactor;

maintaining a mole ratio of aniline to ethylene of from 2 to 10, a temperature from 250° to 400° C.; and maintaining an LHSV of from 0.05 to 0.5 $hr^{-1}$.

2. The process of claim 1 wherein said reaction is carried out at a temperature of from about 300° to 375° C. and a pressure of from 500 to 2000 psig.

3. The process of claim 2 wherein said silica-alumina catalyst contains from 70 to 85% silica by weight.

4. The process of claim 1 wherein said reaction is carried out at a space velocity of 0.1 to 0.25 $hours^{-1}$.

* * * * *